United States Patent [19]
Ohmi et al.

[11] Patent Number: 5,414,361
[45] Date of Patent: May 9, 1995

[54] METHOD OF MEASURING VERY SMALL QUANTITY OF IMPURITY IN GAS

[75] Inventors: Tadahiro Ohmi, 2-1-17-301, Komegafukuro, Aoba-ku, Sendai-city, Miyagi-prefecture; Yoshio Ishihara, Tsuchiura; Ryosuke Fukushima, Kyoto, all of Japan

[73] Assignees: Horiba, Ltd., Kyoto; Nippon Sanso Corporation, Tokyo; Tadahiro Ohmi, Miyagi, all of Japan

[21] Appl. No.: 893,722

[22] Filed: Jun. 5, 1992

[30] Foreign Application Priority Data

Jun. 6, 1991 [JP] Japan .................. 3-163661

[51] Int. Cl.⁶ .................. G01N 27/42; G01N 35/08
[52] U.S. Cl. .................. 324/439; 73/29.02; 436/55; 324/71.1
[58] Field of Search .............. 324/438, 439, 425, 71.1; 73/29.02, 335.02, 61.43; 374/16, 21; 204/153.22, 53.1; 436/55

[56] References Cited

U.S. PATENT DOCUMENTS

| | | | |
|---|---|---|---|
| T961,025 | 4/1969 | Ekiner et al. | 73/61.43 |
| 2,258,045 | 3/1938 | Christie . | |
| 2,350,378 | 6/1944 | Wallace . | |
| 3,318,107 | 5/1967 | Riley et al. | 73/29.02 |
| 3,937,059 | 2/1976 | Nisolle | 374/21 |
| 3,945,905 | 3/1976 | Persson . | |
| 4,216,669 | 8/1980 | Harding, Jr. | 73/29.02 |
| 4,222,247 | 6/1981 | Strain . | |
| 4,227,411 | 10/1980 | Abramovich | 374/21 |
| 4,455,213 | 6/1984 | Neti . | |
| 5,045,163 | 9/1991 | Nyberg et al. | 324/439 |

FOREIGN PATENT DOCUMENTS

| | | | |
|---|---|---|---|
| 895986 | 11/1953 | Germany . | |
| 2932137 | 2/1981 | Germany . | |
| 0130978 | 10/1979 | Japan | 73/29.02 |
| 0044337 | 3/1983 | Japan | 73/29.02 |
| 0306557 | 12/1988 | Japan | 73/335.02 |
| 0493712 | 11/1975 | U.S.S.R. | 73/29.02 |
| 0690418 | 10/1979 | U.S.S.R. | 73/335.02 |
| 8801740 | 3/1938 | WIPO . | |

*Primary Examiner*—Maura K. Regan
*Attorney, Agent, or Firm*—Price, Gess & Ubell

[57] ABSTRACT

A method capable of accurately and inexpensively measuring a very small quantity of impurities, such as water, contained in chemical substances, which are gaseous at normal temperature and pressure, is provided. A concentration of a very small quantity of impurities, contained in the chemical substances, which are gaseous at normal temperature and pressure, is measured by introducing the chemical substances into a cell under the condition of liquefied gases to measure an electric conductivity of the liquefied gases.

6 Claims, 7 Drawing Sheets

METHOD OF MEASURING VERY SMALL QUANTITY OF IMPURITY IN GAS

BACKGROUND OF THE INVENTION

1. Field of the Invention

The present invention relates to a method of measuring a very small quantity of impurities in a gas.

2. Description of the Prior Art

High-purity halogen gases, hydrogen halide gases and inorganic hydrides have been used as dry etching gases in the production of semiconductors. Various kinds of gases such as $SiH_4$, $Si_2H_6$ and $SiH_2Cl_2$, have been used in the formation of thin films of Si, $SiO_2$, $Si_3N_4$ and the like but even though a remarkably very small quantity (for example a ppb-level) of impurities may be contained in these gases, a bad influence upon a manufacturing process of LSI and the like by these impurities is increased as a circuit pattern is reduced to line details and also a gas piping system itself can be seriously influenced. So, it has been desired in the industry to accurately measure any concentration of the impurities at a ppb-level and to control them.

A method of detecting a dew point of a gas to calculate a concentration of impurities on the basis of the dew point has been known as the conventional method of measuring a concentration of very small quantity of impurities, for example water, contained in a gas. For example nitrogen gas, which is one of the inert gases, can be measured until a dew point of $-90°$ C. (about 95 ppb in a concentration of impurities).

However, the halogen gases and inorganic hydrides themselves have high dew points, so that a lower concentration of water has been unable to be detect by the above described method. So, it has been thought to use an atmospheric ionization mass spectrometer (APIMS). Although a remarkably very small quantity of impurities can be measured by APIMS, it is not only expensive but also large-sized, so that a disadvantage has occuured in that an installing site is limited.

In addition, an ionization process by a corona discharge under an atmospheric pressure is comprised, so that a disadvantage has occurred in that a direct measurement is impossible and thus an accurate measurement cannot be achieved due to a corrosion in case of the halogen gases and for example an accumulation of Si and the like in case of reactive gases such as $SiH_4$.

SUMMARY OF THE INVENTION

The present invention has been achieved paying attention to the above described matters and it is an object of the present invention to provide a method of measuring a very small quantity of water in a gas capable of accurately and inexpensively measuring a very small quantity of impurities, such as water, contained in a chemical substance which is gaseous at ordinary temperature and pressure (atmospheric pressure at room temperature). Measuring a very small quantity of impurities in a gas according to the present invention, takes into consideration that chemical substances, such as halogen (for example $F_2$, $Cl_2$ and $Br_2$) or inorganic hydrides (for example HCl, HBr, $NH_3$ or $SiH_4$ and $SiH_2Cl_2$), which are gaseous at ordinary temperature and pressure, are dissociated under the condition of liquefied gases by a presence of water to change an electric conductivity and in also other chemical substances, which are gaseous at ordinary temperature and pressure, water as an impurity is dissociated under the condition of liquefied gases to change the electric conductivity, the chemical substances are introduced into a cell under the condition of liquefied gases to measure the electric conductivity of the liquefied gases.

According to the present; invention, the chemical substances, such as halogen or inorganic hydrides, which are gaseous at ordinary temperature and pressure, are pressurized or cooled to be turned into liquefied gases which are then introduced into a cell to measure the electric conductivity under the condition of liquefied gases, to enable a quantitative determination of the concentration of a very small quantity of impurities, such as water, contained in the chemical substances from a predetermined relation between the concentration (quantity) of for example water contained in the chemical substances and the electric conductivity.

DETAILED DESCRIPTION OF THE PREFERRED EMBODIMENTS

The preferred embodiments of the present invention will be below described with reference to the drawings.

Figure 1:
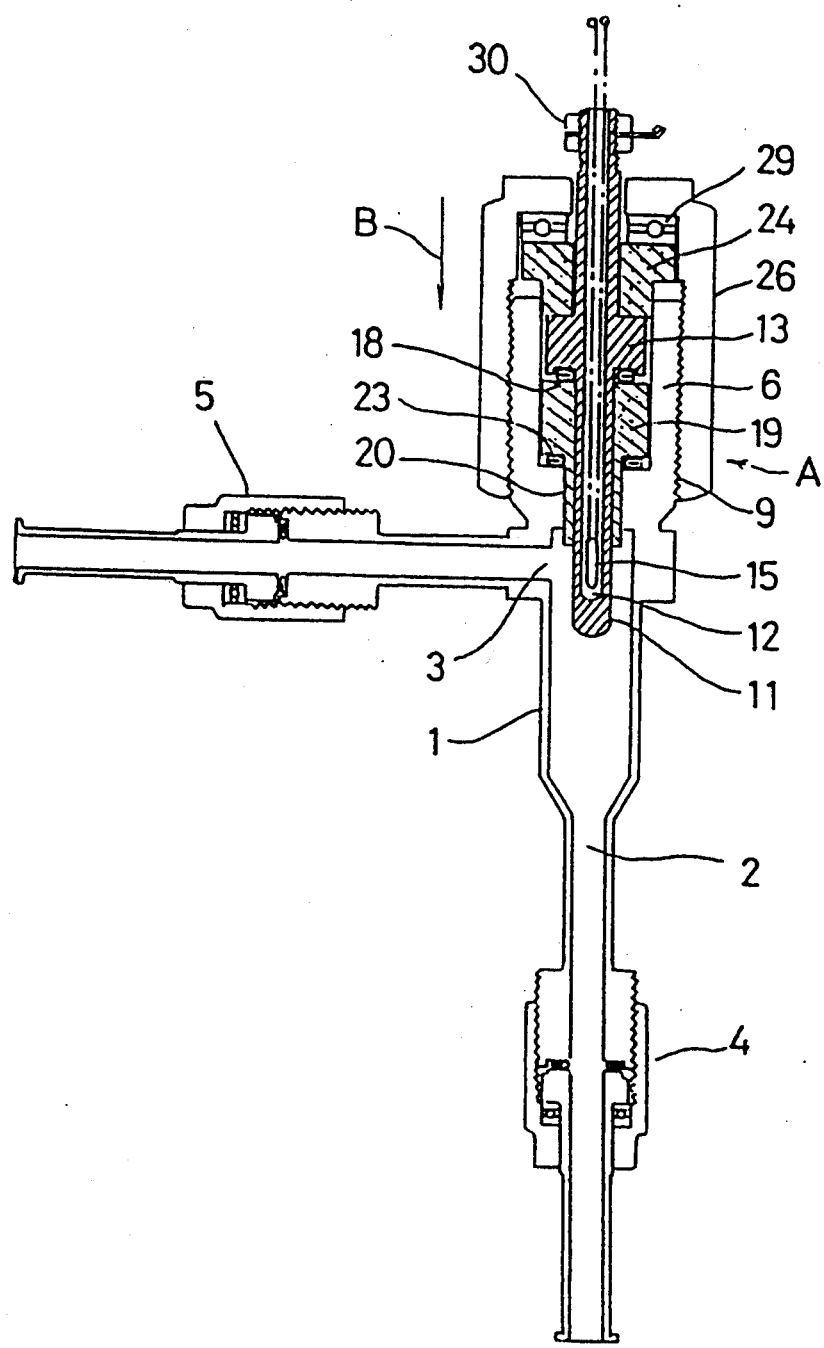
FIG. 1 is a longitudinal sectional view showing one example of a cell for measuring an electric conductivity used in a method of measuring a very small quantity of impurities in a gas according to the present invention.

FIG. 1 is a longitudinal sectional view showing one example of a cell A (hereinafter referred to as a cell) for measuring an electric conductivity used in a method of measuring a very small quantity of impurities in a gas according to the present invention. Reference numeral 1 designates a pressure container serving also as an outer electrode on the side of a lower impedance in an alternating bielectrode method and is provided with an inlet port 2 of a liquefied gas to be measured on a lower side thereof and an outlet port 3 of the liquefied gas on an upper side thereof. The pressure container 1 is made of corrosion resistant metals, such as stainless steels, and an inner surface of the pressure container 1 is subjected to an electro-polishing, an oxidative passivating treatment or a fluorinative passivating treatment to be improved in chemical resistance and corrosion resistance. The pressure container 1 has a highly airtight construction, as described later.

Inlet port 2 is connected with a gas-liquefying apparatus or a liquefied gas cylinder (not shown) through a coupling 4. In addition, the outlet port 3 is connected with pipings to an apparatus for producing semiconductors and the like (not shown) through a coupling 5. A cylindrical member 6 is electrically and mechanically connected with the pressure container 1 and provided with a cylindrical hole 7 opened at one end and is a hole 8 having a diameter smaller than that of the cylindrical hole 7 connected with the cylindrical hole 7 formed therewithin. A tapped portion 9 is formed on an outer circumference thereof, as shown also in FIG. 2. Also an inner surface of the cylindrical member 6 is subjected to an electro-polishing, an oxidative passivating treatment or a fluorinative passivating treatment.

Reference numeral 11 designates an inner electrode arranged concentrically with the pressure container 1 in an upper space within the pressure container 1. That is to say, in a cell measuring an electric conductivity used in a method according to the present invention a measuring electrode is composed of the pressure container 1 serving also as an outer electrode and an inner electrode 11 arranged in a highly insulating connection with the pressure container 1. It is necessary to determine a cell constant of the measuring electrode depending upon a sample but this cell constant, is determined by an inner surface area of the pressure container 1 in a portion wherein the pressure container 1 and the inner electrode 11 are opposite to each other, an area of an outer surface, with which the inner electrode 11 is connected, and a distance from the pressure container 1 to the inner electrode 11.

Figure 2:
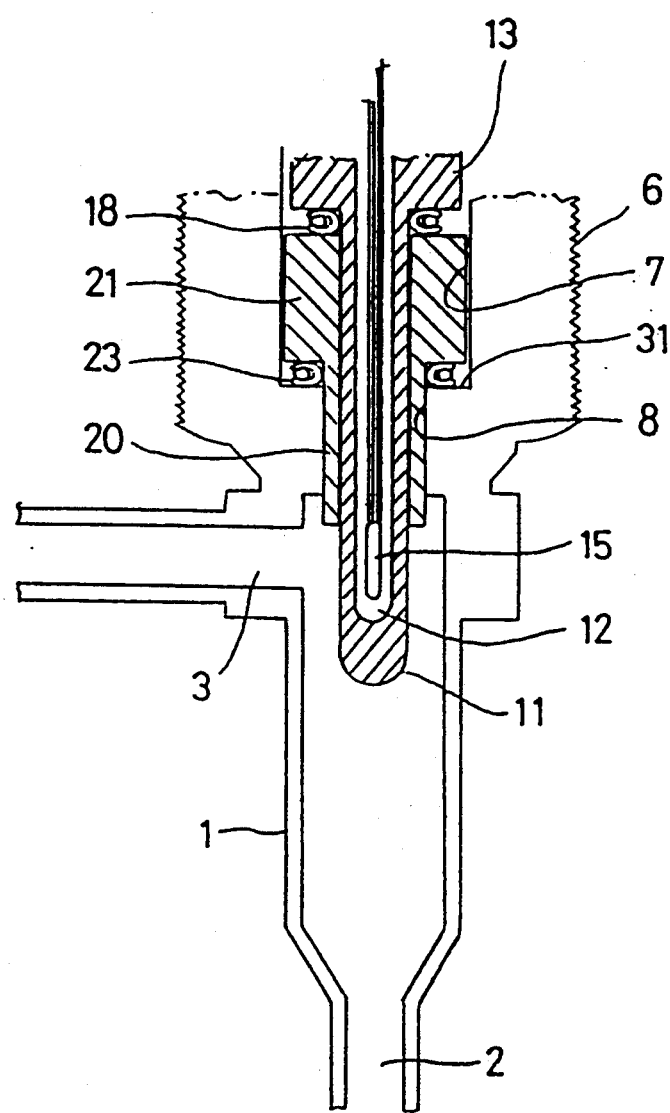
FIG. 2 is a longitudinal sectional view showing a construction of essential parts of the cell.
Figure 3:
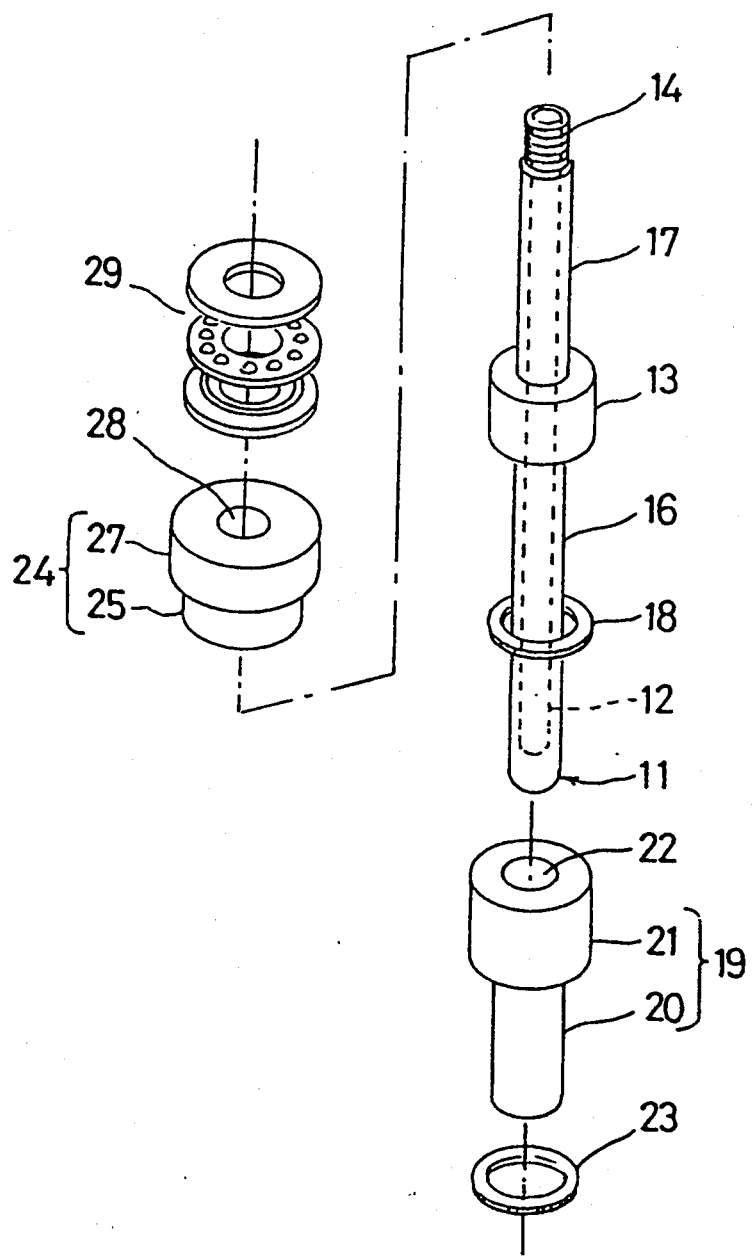
FIG. 3 is an exploded perspective view showing a construction of an internal electrode and a sealing construction.

The inner electrode 11 is, as shown also in FIGS. 2, 3, provided with a hollow member 12 opened on the side of one end and closed on the side of the other end and a diffused-diameter portion 13 having a diameter smaller than an inside diameter of the cylindrical member 6 formed in a midway portion in the longitudinal direction. An outside diameter of the diffused-diameter portion 13 of the inner electrode is set so that a clearance having an appointed high insulating power may be formed between the inner electrode 11 and the inner surface of the cylindrical member 6 under the condition that the inner electrode 11 is arranged within the pressure container 1, as shown in FIG. 1

The inner electrode 11 is made of corrosion resistant metal, such as stainless steel, and the outer surface of the inner electrode 11 is subjected to an electro-polishing, an oxidative passivating treatment or a fluorinative passivating treatment. In addition, the inner electrode 11 is provided with a tapped portion 14 formed at an end portion on the opened side thereof and a temperature sensor 15 is inserted into the hollow member 12 from the opened side until it reaches the vicinity of a closed portion. The temperature sensor 15 is inserted into an inside of the hollow member 12 of the inner electrode 11 and is not brought into direct contact with a liquefied gas, so that it is not necessary to subject the temperature sensor 15 to a chemical resisting treatment, a corrosion-resisting treatment and the like. Furthermore, hereinafter a reduced-diameter portion from the diffused-diameter portion 13 of the inner electrode to an end portion on the closed side is referred to as an inward portion 16 of the inner electrode and a reduced-diameter portion from the increased-diameter portion 13 of the inner electrode to an end portion of the opened side is referred to as an outward portion 17 of the inner electrode.

Reference numeral 18 designates a C-ring as a first sealing ring put on the inward portion 16 of the inner electrode so as to be adjacent to one side of the increased diameter portion 13 of the inner electrode. Reference numeral 19 designates a first stepped insulating spacer put on the inward portion 16 of the inner electrode, composed of a reduced-diameter portion 20 having a diameter slightly smaller than that of the hole 8 formed between the pressure container 1 and the cylindrical member 6 and a diffused-diameter portion 21 having a diameter larger than that of the reduced-diameter-portion 20 but slightly smaller than that of the hole 7 of the inner electrode, and provided with a hole 22 having a diameter slightly larger than that of the inward portion 16 of the inner electrode passing therethrough. The first insulating spacer 19 is made of highly insulating materials, such as ceramics, and an outer surface including both end faces of the first insulating spacer 19 is subjected to a mirror-polishing.

The reduced-diameter portion 20 of the first insulating spacer 19 is, as shown in FIGS. 1, 2, inserted into the hole 8 of the cylindrical member 6 so that a pointed end thereof may arrive at the vicinity of the outlet port 3 of the pressure container 1. Although the cell constant is determined by the areas of the inner and outer electrodes and the distance from the inner electrode to the outer electrode, as above described, it can be regulated also by regulating a length of the reduced-diameter portion 20 of the first insulating spacer 19 in addition to regulating a length of the inner electrode 11. In addition, the reduced-diameter portion 20 reduces a contribution to the cell constant in the portion serving as a stagnant portion of the liquefied gas in the cell by increasing a substantial length between the inner electrode and the outer electrode in the portion positioned above the outlet port 3 within the pressure container 1 to improve an accuracy of measurement of an electric conductivity meter.

Reference numeral 23 designates a C-ring as a second seating ring put on the reduced-diameter portion 20. Reference numeral 24 designates a second insulating spacer put on the outward portion 17 of the inner electrode so as to be adjacent to the other side of the diffused-diameter portion 13 of the inner electrode, composed of a reduced-diameter portion 25 having a diameter slightly smaller than that of the hole 7 of the cylindrical member 6 and a diffused-diameter portion 27 having a diameter larger than that of the reduced-diameter portion 25 but slightly smaller than an inside diameter of a cap nut 26 screwed on the cylindrical member 6, and provided with a hole 28 having a diameter slightly larger than that of the outward portion 17 of the inner electrode passing therethrough. The second insulating spacer 24 is made of highly insulating materials, such as ceramics, and an outer surface including both end faces of the second insulating spacer 24 is subjected to a mirror-polishing. Reference numeral 29 designates a thrust bearing and reference numeral 30 designates a voltage terminal for applying a voltage to the inner electrode 11.

One example of procedures for arranging the inner electrode 11 within the pressure container 1 will be below described. The first sealing ring 18 is put on the inward portion 16 of the inner electrode 11 with the temperature sensor 15 inserted into the hollow member 12 so as to be adjacent to one side of the diffused-diameter portion 13 of the inner electrode and then the first insulating spacer 19 is put on the first sealing ring 18. The second sealing ring 23 is put on the reduced-diameter portion 20 of the first insulating spacer 19 while the second insulating spacer 24 is put on the outward portion 17 of the inner electrode 11 so as to be adjacent to the other side of the diffused-diameter portion 13 of the inner electrode and then the thrust bearing 29 is put on the second insulating spacer 24.

The inner electrode 11, on which the respective members have been put in the above described manner, is inserted into the pressure container 1 with the side of the closed portion as the head through the cylindrical member 6. The cap nut 26 is put on the cylindrical member 6 to be screwed up. When the cap nut 26 is screwed up, a torque in the direction of rotation is released by an action of the thrust bearing 29 and thus a force acts merely in the direction shown by an arrow B in FIG. 1, whereby the first sealing ring 18 is strongly held between one side of the diffused-diameter portion 21 of the first insulating spacer 19 and the diffused-diameter portion 13 of the inner electrode and the second sealing ring 23 between a stepped portion 31 (refer to FIG. 2) of the cylindrical member 6 and the other side of the first insulating space 19 without damaging the sealing portion. As a result, the inner electrode 11 is held within the pressure container 1 concentrically with the pressure container 1 and the rings 18, 23 are evenly deformed to seal up the inner electrode 11 and the first insulating spacer 19 by means of the ring 18 and seal up the cylindrical member 6 of the pressure container 1 and the first insulating spacer 19 by means of the ring 23, whereby maintaining an airtightness within the pressure container 1.

Figure 4:
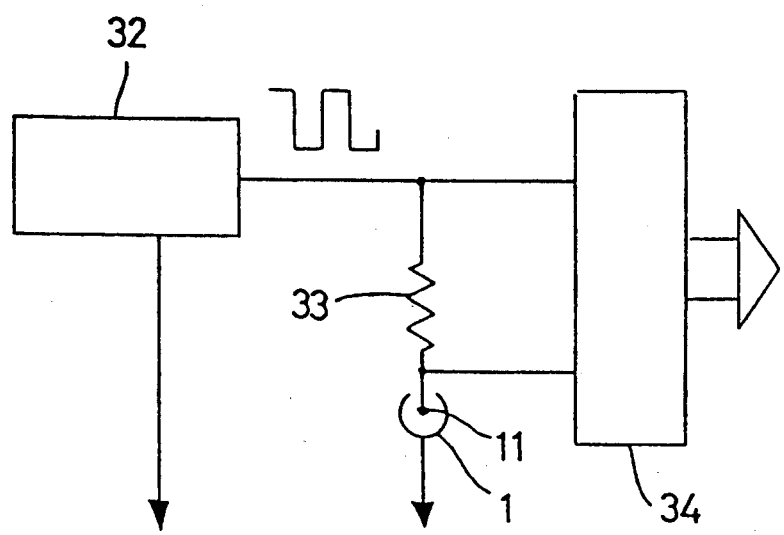
FIG. 4 is a circuit diagram showing one example of an electric construction for placing the method according to the present invention into practice.

FIG. 4 is a circuit diagram for place a method according to the present invention into practice. Referring to FIG. 4, reference numeral 32 designates a transmitter transmitting an alternating voltage of for example about 900 Hz which is applied between the inner electrode 11 and the pressure container 1 serving also as the outer electrode. In addition, reference numeral 33 designates a fixed resistance. Voltages at both ends of said fixed resistance 33 are put in a processor 34 as detected outputs.

Figure 5:
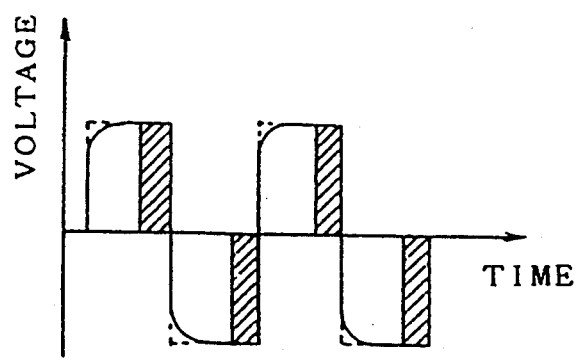
FIG. 5 is a diagram showing one example of a detected output.

FIG. 5 shows one example of the detected outputs. However, in the case where the pressure container 1 is made of the stainless steel, if the alternating voltage of about 900 Hz is applied between the inner electrode and the outer electrode in the above described manner, the detected outputs are influenced by a dielectric constant to deteriorate a surmounting, whereby resulting an error. In order to prevent this, for example it is thought to coat the inner surface of the pressure container 1 with platinum but this is expensive.

So, according to the present invention, in the processor 34 a synchronism with a transmission frequency is conducted so as not to adopt portions, of which its wave form is disturbed, as signals and to take out merely the shaded portions in FIG. 5 as signals, whereby solving a problem that the surmounting is deteriorated. In addition, such a taking-out of signals is effective also in the case where the inner surface of the pressure container 1 is subjected to the electro-polishing and the like taking the corrosion resistance and the chemical resistance into consideration.

Figure 6:
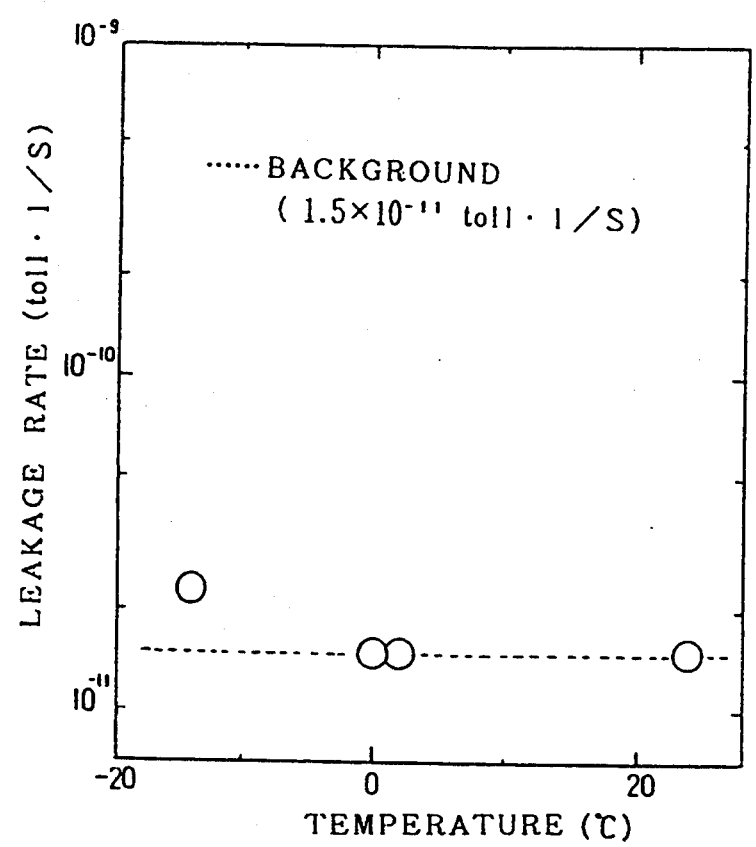
FIG. 6 is data showing the external leak rate of the cell.

FIG. 6 is data showing measured results on an airtightness of a cell A used in the method according to the present invention. As shown in FIG. 6, the cell A exhibits a slight increase of leakage rate at $-10°$ C. or less but this does not have substantial influence upon the measurement, that is it is found that the cell A is remarkably superior in airtightness. In addition, a plot at the leak rate of $1.5 \times 10^{-11}$ Torr·l/s shows a detection limit of a He leak detector.

In addition, in the case where the airtightness within the pressure container 1 is insufficient, not only liquefied gases introduced into the pressure container 1 are leaked out but also water outside of the pressure container 1 is diffused into the pressure container 1 by a differential concentration. As a result, not only an error of measurement is produced but also the piping system incorporated in the pressure container 1 is damaged.

Figure 7:
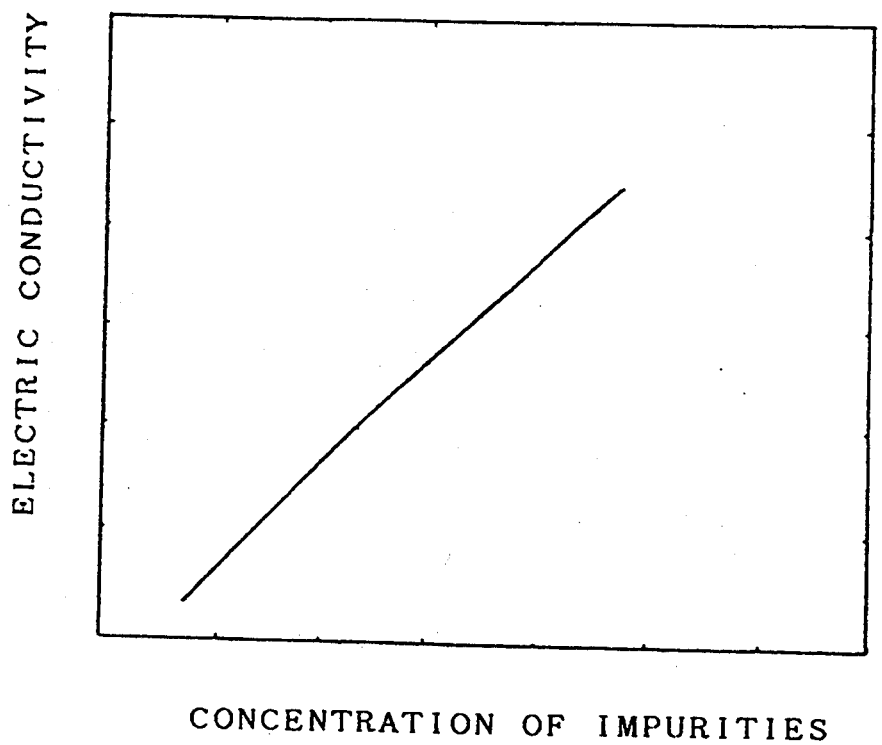
FIG. 7 is a diagram showing a relation between a concentration of impurities and an electric conductivity in case of liquefied hydrogen chloride.

In a process, in which the liquefied gases are introduced into and guided out from the pressure container 1, their electric conductivity is measured by means of the pressure container 1 and the inner electrode 11 but the measured electric conductivity can be easily converted into a concentration of impurity by data showing for example a relation between a concentration of impurity in liquefied halogen gases and an electric conductivity with a logarithm of concentration of water as an axis of abscissa and a logarithm of electric conductivity as an axis of ordinate, as shown in FIG. 7, and thus a concentration of a very small quantity of impurities contained in the liquefied gases can be measured.

Because, in the case where water exists in the liquefied gases, such as liquefied hydrogen chloride, the electric conductivity is greatly changed due to the dissociation as shown by the following chemical equation (1). In addition, it goes without saying that the electric conductivity is greatly changed due to the dissociation of merely water.

$$HCl + H_2O \rightleftharpoons H_3O^+ + Cl^- \tag{1}$$

In addition, in the case where the impurities, such as $H_2SO_4$ and $SiO_2$, exist in liquefied hydrogen chloride, water is produced to be dissociated in the same manner as above described, as shown by the following chemical equations (2), (3), whereby greatly changing the electric conductivity, and thus the concentration of impurities, such as $H_2SO_4$ and $SiO_2$, can be measured in the form of a value converted into water.

$$H_2SO_4 HCl \rightleftharpoons HSO_3Cl + H_2O \tag{2}$$

$$SiO_2 + 4HCl \rightleftharpoons SiCl_4 + 2H_2O \tag{3}$$

Figure 8:
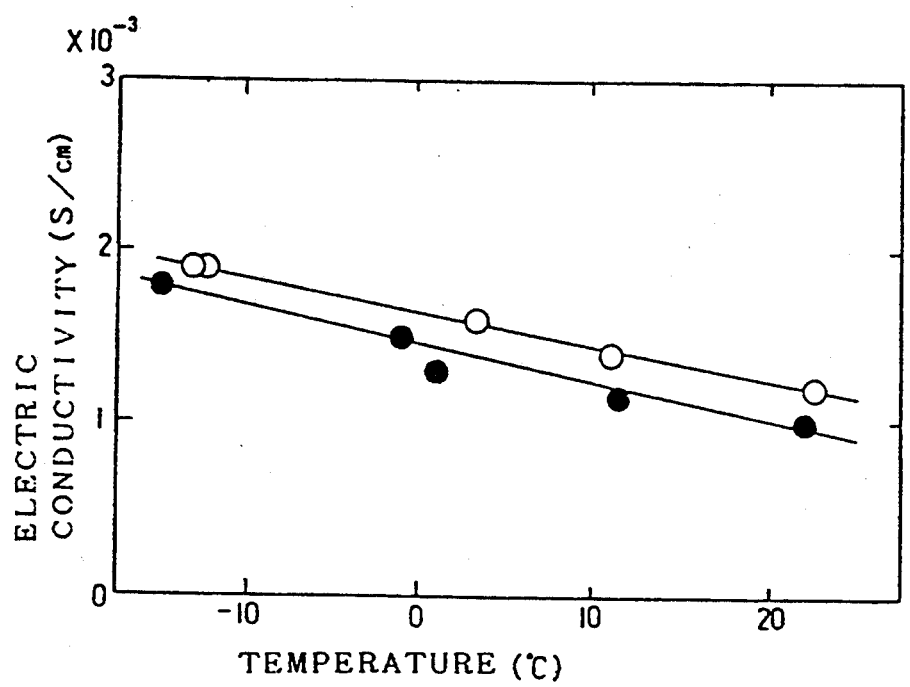
FIG. 8 is a diagram showing a relation between a temperature and an electric conductivity in case of liquefied hydrogen chloride.

Furthermore, FIG. 8 plots a relation between a temperature and an electric conductivity for two kinds liquefied hydrogen chloride gas. In order to liquefy chemical substances which are gaseous at normal temperature and pressure, they are pressurized or cooled but the electric conductivity is changed with a temperature-change, as shown in FIG. 8, so that it is desirable to keep the temperature constant or compensate the electric conductivity by the use of the data showing the relation between a temperature and an electric conductivity for the liquefied hydrogen chloride gas as shown in for example FIG. 8.

According to the above described preferred embodiment, the chemical substances, which are gaseous at normal temperature and pressure, are pressurized or cooled to be turned into liquefied gases and then introduced into the pressure container 1 serving also as the outer electrode followed by measuring the electric conductivity of said liquefied gases by means of the pressure container 1 and the inner electrode provided within the pressure container 1 concentrically with the pressure container 1, whereby quantitatively determining the concentration of impurities in the liquefied gases from the previously determined relation between a concentration (quantity) of impurities in the chemical substances and an electric conductivity, so that a very small quantity of water or impurities, such as $H_2SO_4$ and $SiO_2$, producing water by a reaction can be measured accurately and inexpensively as compared with the conventional method.

In addition, not only the pressure container 1 is made of corrosion-resisting metal but also the inner surface of the pressure container 1 and the outer surface of the inner electrode 11 are subjected Lo the electro-polishing, the oxidative passivating treatment or the fluorinative passivating treatment, so that, even though the impurities are contained in the liquefied gaseous, the impurities are not adsorbed on and desorbed from the pressure container 1 and the inner electrode 11 as measuring electrodes and the cell A itself does not generate impurities and additionally also corrosive gases can be adopted as an object to be measured.

And, according to the above described preferred embodiment, in the cylindrical member 6 connected with the pressure container 1 the first sealing ring 18 and the first stepped insulating spacer 19 are put on one side of the inner electrode 11 so that the first sealing ring 18 may be closer to the diffused-diameter portion 13 of the inner electrode. The second sealing ring 23 is put on the reduced-diameter portion 20 of the first insulating spacer 19, the second stepped insulating spacer 24 and the thrust bearing 29 being put on the other side of the inner electrode 11 so that the second insulating spacer 24 may be closer to the diffused-diameter portion 13 of the inner electrode. The cap nut 27 screwed on the cylindrical member 6 so that the first sealing ring 18 between the first insulating spacer 24 and the diffused-diameter portion 13 of the inner electrode and the second sealing ring 23 is between the stepped portion 31 of the cylindrical member 6 and the first insulating spacer 24, so that high airtightness can be kept within the pressure container. For example, the leak rate is reduced to the detecting limit (about $1.5 \times 10^{-11}$ Torr·l/s or less) of the He leak detector and thus not only the liquefied gas can be prevented from being leaked out of the pressure container 1 but also gases can be prevented from entering the pressure container 1 from outside.

In addition, since the thrust bearing 29 is provided between the cap nut 27 and the second insulating spacer 24, an advantage occurs also in that the rotary force of the cap nut 27 does not directly act upon the second insulating spacer 24.

As above described, according to the method of the present invention, a very small quantity of impurities contained in the chemical substances, which are gaseous at normal temperature and pressure, can be measured accurately and inexpensively.

What is claimed is:

1. A method of measuring a very low level of impurities in a substance that is normally gaseous at room temperature and pressure and is used in the manufacture of semiconductor chips (LSI) after being tested, comprising the steps of:
    providing a gas sample comprising a substance that is a gas at room temperature and atmospheric pressure;
    providing a test cell having two electrodes for receiving the gas sample;
    liquefying the gas sample by cooling below room temperature or pressurizing above atmospheric pressure;
    introducing the liquefied gas sample into the test cell;
    measuring the temperature of the liquefied gas sample;
    applying an alternating voltage to a first test cell electrode through a fixed resistance and at a predetermined frequency;
    connecting a second test cell electrode to ground;
    receiving, from the first electrode, an alternating output signal representative of the electrical conductivity;
    sampling the alternating output signal to provide a square wave of lesser width, thereby avoiding a leading edge of the output signal;
    determining the level of impurities in the liquefied gas sample by reference to the conductivity at a given temperature.

2. The method of claim 1 wherein the step of measuring further includes comparing a logarithm of measured electrical conductivity with a logarithm of the conductivity of known concentrations of water in the liquefied gas sample.

3. The method of claim 1 wherein the step of measuring further includes comparing a logarithm of measured electrical conductivity with a logarithm of the conductivity of known concentrations of water in the liquefied gas sample.

4. A method of measuring the quantity of impurities in a sample of gas that is normally gaseous at room temperature and atmospheric pressure by measuring the water content of the sample, the sample gas is used in the production of semiconductor components, the method comprising the steps of:
    providing a gas sample selected from a group consisting of a halogen gas, a hydrogen halide gas, an inorganic hydride gas and an inorganic hydrogen halide gas;
    providing a gas-tight test cell for receiving the gas sample;
    liquefying the gas sample before introducing it to the test cell;
    applying an electrical signal to the liquefied gas sample in the test cell;
    measuring an electrical characteristic of the gas sample in the test cell generated by the electrical signal that is influenced by the quantity of water in the liquefied gas sample;
    determining the actual electrical conductivity of the liquefied gas sample from the electrical characteristic; and
    determining the quantity of impurities in the sample gas from a predetermined relationship of electrical conductivity and the impurities.

5. The method of claim 4 wherein the test cell has two electrodes and the step of measuring includes:
    applying an alternating voltage to the first test cell electrode through a fixed resistance and at a predetermined frequency;
    connecting the second electrode to ground;
    receiving, from the first electrode, an alternating output signal representative of the electrical conductivity; and
    sampling the alternating output signal to provide a square wave of lesser width, thereby avoiding a leading edge of the output signal.

6. The method of claim 4 wherein the test cell provided to receive the liquefied gas sample has a leakage rate no greater than $1.5 \times 10^{-11}$ Torr·l/s.

* * * * *